United States Patent [19]

Duffett

[11] Patent Number: Plant 5,351

[45] Date of Patent: Nov. 20, 1984

[54] CHRYSANTHEMUM PLANT NAMED SURFINE

[75] Inventor: William E. Duffett, Salinas, Calif.

[73] Assignee: Yoder Brothers, Inc., Barberton, Ohio

[21] Appl. No.: 467,859

[22] Filed: Feb. 18, 1983

[51] Int. Cl. ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Surfine having flat capitulum form; decorative capitulum type; light yellow ray floret color; diameter across face of capitulum ranging from 70 to 85 mm. at maturity; uniform eight week photoperiodic flowering response to short days; short plant height when grown as a pinched, spray pot mum, and semi-spreading branching

3 Drawing Figures

1

The present invention comprises a new and distinct cultivar of *Chrysanthemum morifolium,* Ramat., named Surfine.

Surfine is a product of a planned sport induction program which had the objective of creating new chrysanthemum cultivars that would expand the color range on existing cultivars while retaining their other original traits.

Surfine was discovered and selected by Williami E. Duffett on Apr. 7, 1980 in a controlled environment in Salinas, Calif. as one flowering plant, a color variant within a flowering block established as rooted cuttings from stock plants which had been exposed as unrooted cuttings to an X-ray source of 900 rads. The irradiated variety was Surf, disclosed in U.S. Plant Pat. No. 4,585 and originated by the present inventor.

The first act of asexual reproduction of Surfine was accomplished when vegetative cuttings were taken from the initial selection in July 1980 in a controlled environment in Salinas, Calif. by a technician working under formulations established and supervised by William E. Duffett. Horticultural examination of selected units initiated October 1980 has demonstrated that the combination of characteristics as herein disclosed for Surfine are firmly fixed and are retained through successive generations of asexual reproduction.

Surfine has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Surfine which in combination distinguish this chrysanthemum as a new and distinct cultivar.

(1) Flat capitulum form;

(2) Decorative capitulum type;

(3) Light yellow ray floret color;

(4) Diameter across face of capitulum ranging from 70 to 85 mm. at maturity;

(5) Uniform eight week photoperiodic flowering response to short days;

(6) Short plant height, requiring 1–2 long day weeks prior to pinch and short days, and 1–2 applications of

2

2500 ppm B-9 after the beginning of short days to attain a flowered plant height of 25 to 35 cm., and (7) Semi-spreading branching pattern.

The accompanying photographic drawings depict typical foliage and inflorescence characteristics of Surfine. Sheet 1 is a color photograph of Surfine grown as a pinched spray pot mum, with colors being as accurate as possible with renditions of this type. Sheet 2 is a black and white photograph of three views of the inflorescence of Surfine. Sheet 3 shows the leaves of Surfine in three stages of development (mature, intermediate and immature).

Of the many commercial cultivars known to the present inventor, the most similar in comparison to Surfine is Yellow Torch, disclosed in U.S. Plant Pat. No. 3,421. Reference is made to attached Chart A which compares certain characteristics of Surfine to those same characteristics of Yellow Torch and the parent cultivar Surf.

Yellow Torch differs from Surfine by exhibiting deeper color, a far more upright branching pattern and slower flowering response by one week. Yellow Torch and Surfine are similar in capitulum form and type, capitulum diameter and plant height.

The parent cultivar Surf displays a larger flower and approximately five days faster flowering response.

In the following description, color references are made to The Royal Horticultural Society Colour Chart. The color values were determined between 1:30 P.M. and 2:00 P.M. on Aug. 13, 1982 under 150 foot-candle light intensity at Salinas, Calif.

CLASSIFICATION

Botanical: *Chrysanthemum morifolium,* Ramat., cv SURFINE

Commercial: Disbud and spray decorative pot mum.

INFLORESCENCE

Capitulum:

*Form.*—Flat.

*Type.*—Decorative.

*Diameter across face.*—70 To 85 mm.

Corolla of ray florets:

*Color (general tonality from a distance of three meters).*—Light yellow.

*Color (abaxial).*—4B.

*Color (adaxial).*—6D.

*Shape.*—Oblong. Rounded tip. Frequently spoon shaped.

Corolla of disc florets:

*Color (mature).*—154B.

*Color (immature).*—154A.

Reproductive organs:

*Androecium.*—Present disc florets only; very few; scant pollen.

*Gynoecium.*—Present both ray and disc florets.

PLANT

General appearance:

*Height.*—Short; 25 to 35 cm. given 2 long day weeks before pinch and lights out, and 1-2 applications of 2500 ppm B-9 SP after lights out.

*Branching pattern.*—Prolific. Semi-spreading.

Foliage:

*Color (abaxial).*—147A.

*Color (adaxial).*—147B.

*Shape.*—Deeply lobed. Moderately serrated.

CHART A

COMPARISON OF SURFINE, YELLOW TORCH AND SURF

| CULTIVAR | RAY FLORET COLOR | CAPITULUM FORM AND TYPE | BRANCHING PATTERN |
|---|---|---|---|
| SURFINE | LIGHT YELLOW | FLAT DECORATIVE | SEMI-SPREADING |
| YELLOW TORCH | DARK YELLOW | FLAT DECORATIVE | UPRIGHT |
| SURF | (sometimes tinged bronze) WHITE | FLAT DECORATIVE | SEMI-SPREADING |

CHART A-continued

COMPARISON OF SURFINE, YELLOW TORCH AND SURF

| CULTIVAR | DIAMETER ACROSS FACE OF CAPITULUM | PLANT HEIGHT | FLOWERING RESPONSE PERIOD |
|---|---|---|---|
| SURFINE | 70 to 85 mm. | SHORT 25 to 35 cm. | 8 WEEKS |
| YELLOW TORCH | 70 to 85 mm. | SHORT 25 to 35 cm. | 9 WEEKS |
| SURF | 65 to 95 mm. | SHORT 25 to 35 cm. | 8 WEEKS |

COMPARISONS MADE OF PLANTS GROWN AS PINCHED SPRAY POT MUMS IN SALINAS, CALIFORNIA AND LEAMINGTON, CANADA

I claim:

1. A new and distinct cultivar of *Chrysanthemum morifolium*, Ramat., named Surfine, as described and illustrated, and particularly characterized as to uniqueness by the combined characteristics of flat capitulum form; decorative capitulum type; light yellow ray floret color; diameter across face of capitulum ranging from 70 to 85 mm. at maturity; uniform eight week flowering photoperiodic response; short plant height, and semi-spreading branching pattern.

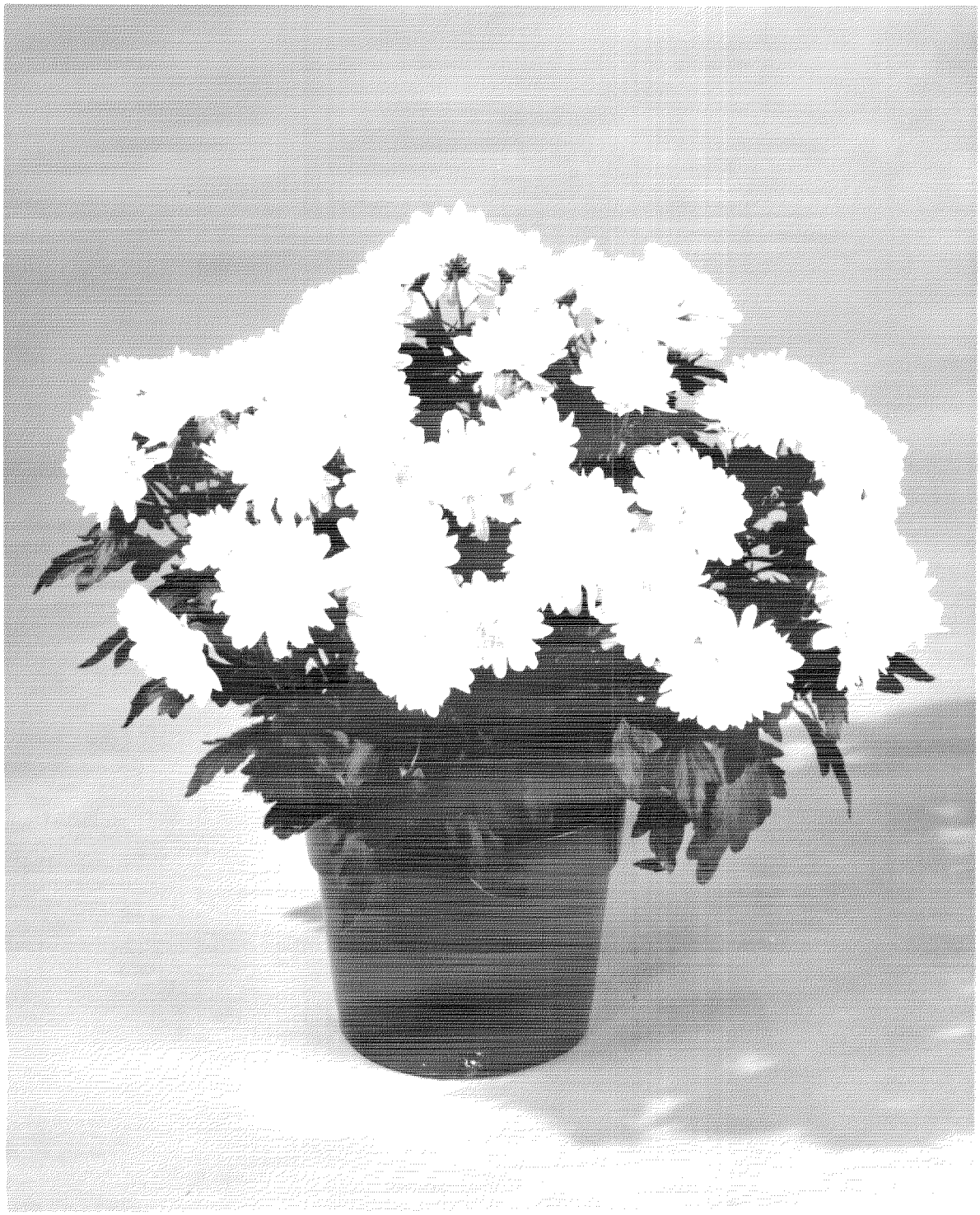

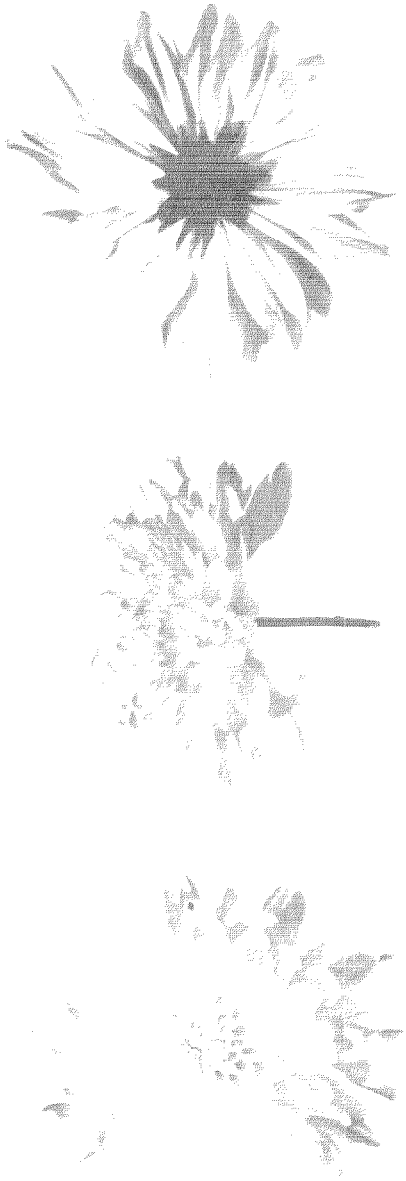

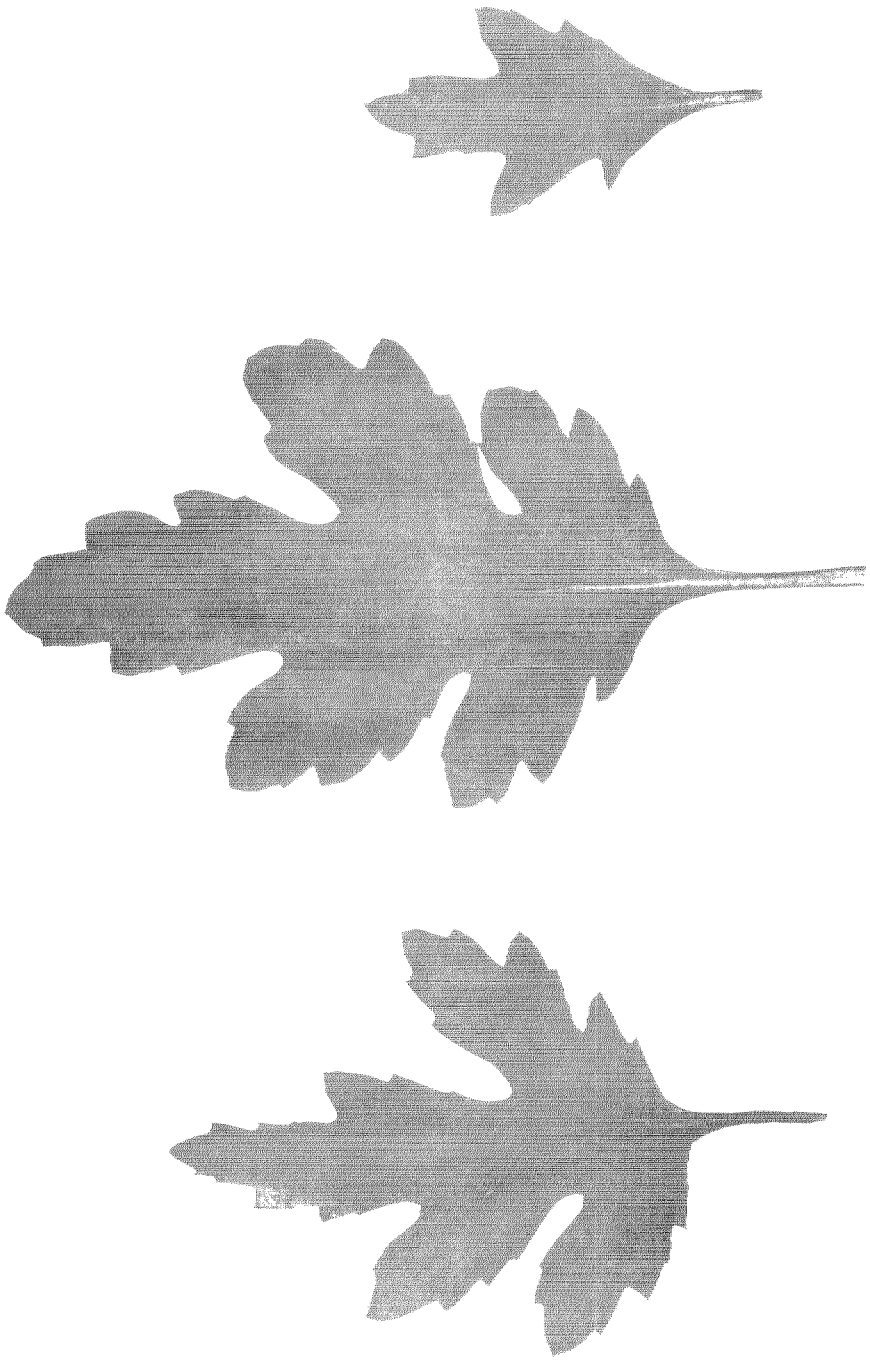

* * * * *